US012653473B2

(12) United States Patent (10) Patent No.: US 12,653,473 B2
Schmidt et al. (45) Date of Patent: Jun. 16, 2026

(54) SYSTEM AND METHOD FOR STABILIZATION OF AN IMAGING POSITIONER USING AN ACTIVE MASS DAMPER

(71) Applicant: Omega Medical Imaging, LLC, Sanford, FL (US)

(72) Inventors: Jeffrey C. Schmidt, Orlando, FL (US); Christopher Henning, Deltona, FL (US); Matthew Skelley, Orlando, FL (US)

(73) Assignee: OMEGA MEDICAL IMAGING, LLC, Sanford, FL (US)

( * ) Notice: Subject to any disclaimer, the term of this patent is extended or adjusted under 35 U.S.C. 154(b) by 406 days.

(21) Appl. No.: 18/514,450

(22) Filed: Nov. 20, 2023

(65) Prior Publication Data

US 2025/0160772 A1 May 22, 2025

(51) Int. Cl.
*A61B 6/00* (2024.01)

(52) U.S. Cl.
CPC ............ *A61B 6/4441* (2013.01); *A61B 6/447* (2013.01); *A61B 6/4476* (2013.01)

(58) Field of Classification Search
CPC ...... A61B 6/4441; A61B 6/447; A61B 6/4476
See application file for complete search history.

(56) References Cited

U.S. PATENT DOCUMENTS 6,574,499 B1 * 6/2003 Dines ................... A61B 8/0825
                                                            128/915
2023/0000457 A1 * 1/2023 Tian ....................... A61B 6/547

OTHER PUBLICATIONS

Koutsoloukas, Lefteris, et al., "Passive, semi-active, active and hybrid mass dampers: A literature review with associated applications on building-like structures", Science Direct, Developments in the Built Environment 12, (2022), 26 pages.
"How does an active mass damper work?", [retrieved online Nov. 20, 2023] <https://isaacantisismica.com/en/how-does-an-amd/>.

* cited by examiner

*Primary Examiner* — Dani Fox
(74) *Attorney, Agent, or Firm* — Tucker Ellis LLP

(57) ABSTRACT

An active mass damper system includes one or more sensors configured to detect motion of a C-arm and output corresponding motion data representative of the motion of the C-arm. A mass damper assembly within the C-arm includes a linear motor, and a mass coupled to the linear motor. The active mass damper system further includes a controller configured to receive the motion data, process the motion data by applying one or more filters to the motion data to create filtered motion data, and control the linear motor, based on the filtered motion data and motor control tuning parameters, to move the mass in a linear reciprocating path to provide a force having a magnitude and a phase configured to dampen at least a portion of the movement of the C-arm.

20 Claims, 8 Drawing Sheets

200 controller
202

Filter → Phase adjustment → Position

↓

PID

↓

Motor Control Tuning

Sensor(s)

206

C-arm    16

Motor Driver — 204

Linear Motor — 212
210

Fan

208 mass — 214

400

402

404 —

406 —

SYSTEM AND METHOD FOR STABILIZATION OF AN IMAGING POSITIONER USING AN ACTIVE MASS DAMPER

FIELD OF INVENTION

The present invention relates to an imaging device, and more particularly to movement and control of the imaging device.

BACKGROUND

Medical imaging of a patient can utilize various different structures in supporting, moving, and aligning the imaging equipment with respect to the patient. One such structure is a C-arm. A C-arm positioner is designed to move, i.e. articulate in various axes of motion. As a result, unintentional, residual motions, e.g. oscillations and vibrations may occur after motions have been commanded to stop. These undesired, residual motions can range from minor vibrations to large bounces, and can negatively affect image quality because the image column is moving with respect to the patient frame of reference. The C-arm position can also change the center of gravity, and loading of the structure which affects the resonant frequency of the C-arm, thus changing the frequency of oscillations. Therefore, it would be desirable to enable the adaptable dampening of undesired motions, such as vibrations, when move commands are executed and the C-arm moves or stops.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more techniques and systems described herein can be utilized to provide an active mass damper system, that includes one or more sensors configured to detect motion of a C-arm and output corresponding motion data representative of the motion of the C-arm. The active mass damper system further includes a mass damper assembly that includes a linear motor and a mass coupled to the linear motor. The active mass damper system also includes a controller configured to receive the motion data, process the motion data by applying one or more filters to the motion data to create filtered motion data, and control the linear motor, based on the filtered motion data and motor control tuning parameters, to move the mass in a linear reciprocating path to provide a force having a magnitude and a phase configured to dampen at least a portion of the motion of the C-arm.

In one aspect, a method for operating an active mass damper system includes receiving motion data from one or more motion sensors located in a C-arm, wherein the motion data is representative of motion of the C-arm, processing the motion data by applying one or more filters to the motion data to create filtered motion data, and controlling a linear motor, based on the filtered motion data and motor control tuning parameters, to move a mass in a linear reciprocating path to provide a force having a magnitude and a phase configured to dampen at least a portion of the motion of the C-arm.

To the accomplishment of the foregoing and related ends, the following description and drawings set forth certain illustrative aspects and implementations. These are indicative of but a few of the various ways in which one or more aspects may be employed. Other aspects, advantages and novel features of the disclosure will become apparent from the following detailed description when considered in conjunction with the drawings.

DETAILED DESCRIPTION

Figure 1:
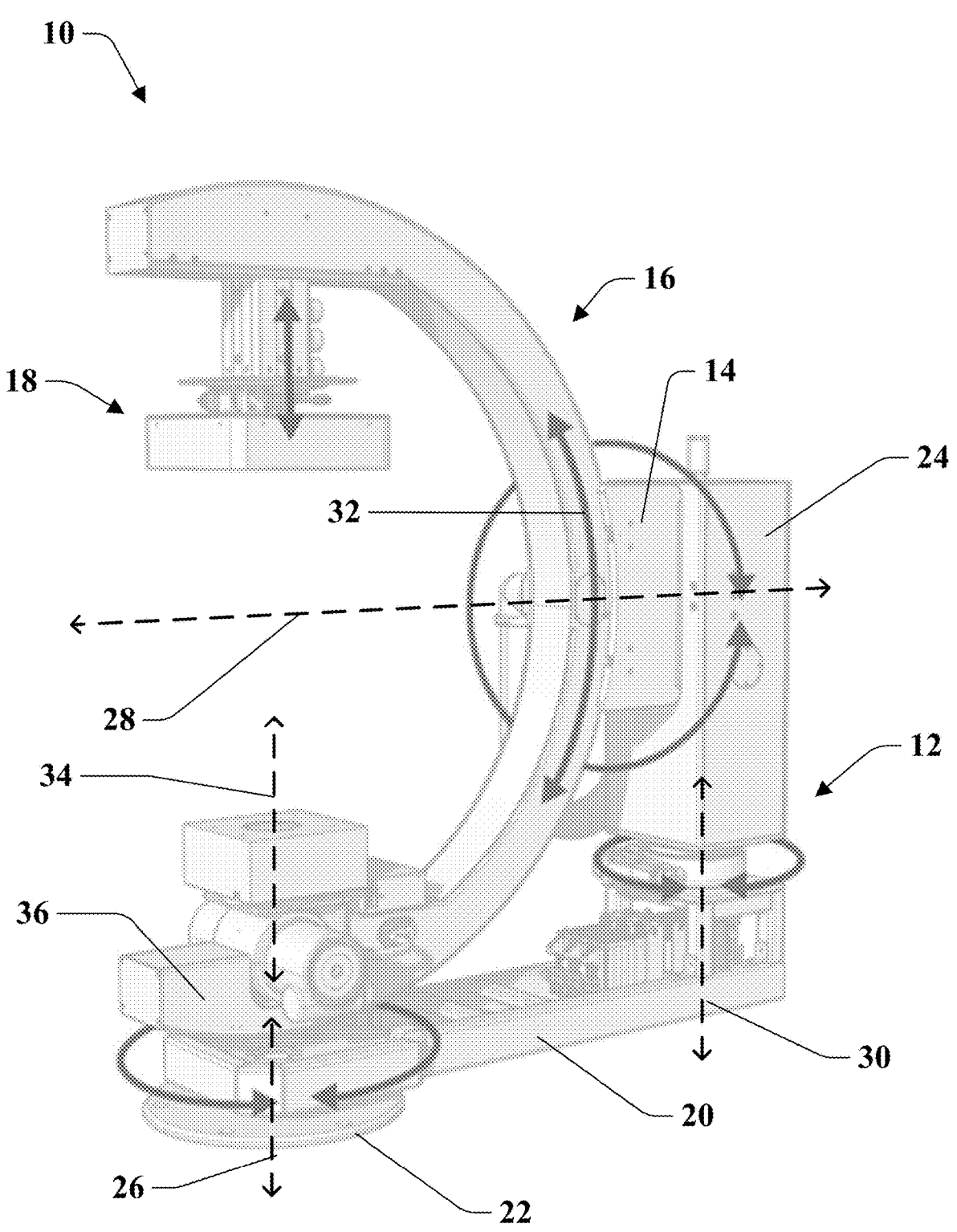
FIG. 1 is a representative view of a C-arm structure, where one or more techniques and/or one or more systems described herein may be implemented.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A C-arm imaging device can include an active mass damper system that includes a mass damper assembly located within a portion of the body of the C-arm. The mass damper system includes a controller configured to monitor movement information related to the C-arm and control a motor within the mass damper assembly to move a mass within the mass damper assembly based on the movement information. The controller can control the motor, for example, to reciprocate the mass back and forth in order to dampen any unwanted movement of the C-arm.

Turning now to FIG. 1, an imaging system is shown generally at reference numeral 10. The imaging system includes an attachment arm 12, sometimes referred to as an L-arm, a pivot assembly 14 rotatably attached to the attachment arm 12, and a C-arm 16 attached to the pivot assembly 14. The imaging system 10 further includes an imaging device 18 attached to the C-arm 16 to rotate with the C-arm 16 and move relative to the C-arm 16. In various embodiments, the imaging device 18 can include an x-ray detector and/or an x-ray source. The attachment arm 12 includes a lower portion 20 having a base 22 rotatably attached to a floor of a room, and an upper portion 24 extending upward from the lower portion 20. The base 22 is rotatable about a first axis 26 perpendicular to the floor to move the attachment arm 12 around a patient. The upper portion 24 can be rotatable about a third axis 30, with respect to the lower portion 20.

The pivot assembly 14 is attached to the upper portion 24 of the attachment arm 12 in a suitable manner to rotate about a second axis 28 extending through the pivot assembly 14 parallel to the floor. The pivot assembly 14 rotates relative to the upper portion 22 to rotate the C-arm 16 and the imaging device 18 around the patient. The imaging device 18 is attached to C-arm 16, which is slidably attached to the pivot assembly 14 in a suitable manner that allows the imaging device 18 to move along an arc 32 relative to the pivot assembly 14. A patient table can be positioned near the imaging device 18, and the imaging device 18 moved relative to the table.

An imaging device design that incorporates a C-arm 16 with an extended cantilevered "L" (e.g. attachment arm 12) allow full access and articulation of the C-arm 16 to both sides of a table. However, an inherent challenge of this type of design is the stability of the attachment arm 12 and C-arm 16 structures due to the extended cantilever and unintended motion due to acceleration and de-acceleration of C-arm 16 angulation and roll axes during and after commanded movements, especially in the vertical C-arm axis 34. It should be appreciated that the C-arm axis 34 is represented by the axis extending vertically from a bottom of the C-arm 16, and which moves with the C-arm 16 such that when the C-arm 16 rolls or otherwise changes position, the C-arm axis 34 remains fixed with respect to the C-arm. For example, once a commanded movement of the C-arm 16 is stopped, the C-arm 16 may continue to have undesired movements such as vibrations or bounce. A contributor to this problem is the inherent flexibility of the structural materials from which the components of the imaging system 10 is constructed, such as steel and aluminum. Often, aluminum is used extensively in the construction of the imaging system 10 because it is relatively lightweight, but more flexible. Furthermore, the C-angulation and roll position affect the flexibility of the machine, and variabilities due to manufacturing tolerances affect the resonant frequency and amplitude of undesired motions of the C-arm 16, thereby reducing the effectiveness of a passive mass damper.

A significant challenge in mitigating undesired motion is that it is difficult to directly measure small undesired perturbations of the C-arm 16 with respect to the room or table frame of reference. Small movements (typically oscillatory perturbations) can negatively affect the imaging process due to movement of the imaging device 18 with respect to the patient, causing blurry images. To address this problem, an active mass damper system 200 is integrated into the imaging system 10.

Figure 2:
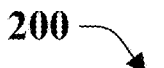
FIG. 2 is a schematic diagram showing components of an active mass damper system.

Turning now to FIG. 2, the active mass damper system 200 includes a controller 202. The controller 202 can be implemented with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The controller 202 may be a microprocessor, but in the alternative, the controller 202 may be any processor, controller, microcontroller, or state machine. The controller 202 may also be implemented as a combination of computing devices, for example a combination of a DSP and a microprocessor, a plurality of microprocessors, multi-core processors, one or more microprocessors in conjunction with a DSP core, or any other such configuration.

The controller 202 can be configured to interact with a motor driver 204 and a mass damper assembly 210 that includes a linear motor 212 configured to move a mass 214 in an reciprocating linear path. The mass damper assembly 210 can be located within the C-arm 16. In one embodiment, the mass damper assembly 210 can be located within a compartment located in the bottom tip 36 of the C-arm 16 as shown in FIG. 1. In certain embodiments, the active mass damper system 200 can also include a fan 208 positioned such that the fan 208 provides a cooling effect on the linear motor 212. The active mass damper system 200 further includes one or more sensors 206 located within the C-arm 16. In certain embodiments, the one or more sensors 206 are one or more accelerometers.

The controller 202 is configured to acquire motion data related to the C-arm 16 from the one or more sensors 206. Communication between the controller 202 and the one or more sensors 206 can be wired or wireless. In an embodiment, the one or more sensors 206 are one or more accelerometers, and the motion data is acceleration data of the C-arm 16. The controller 202 is further configured to filter the acceleration values to remove inherent noise and high frequency vibrations as well as the values associated with intentional commanded movements. In certain embodiments, angular position data from the C-arm 16 positioner can be used to remove the gravity vector from the motion data.

Figure 3:
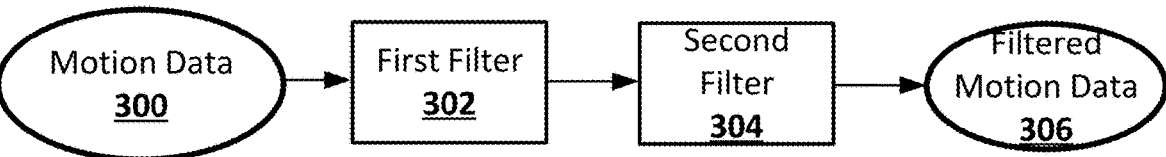
FIG. 3 is a flow diagram depicting processing of accelerometer data.
Figure 4A:
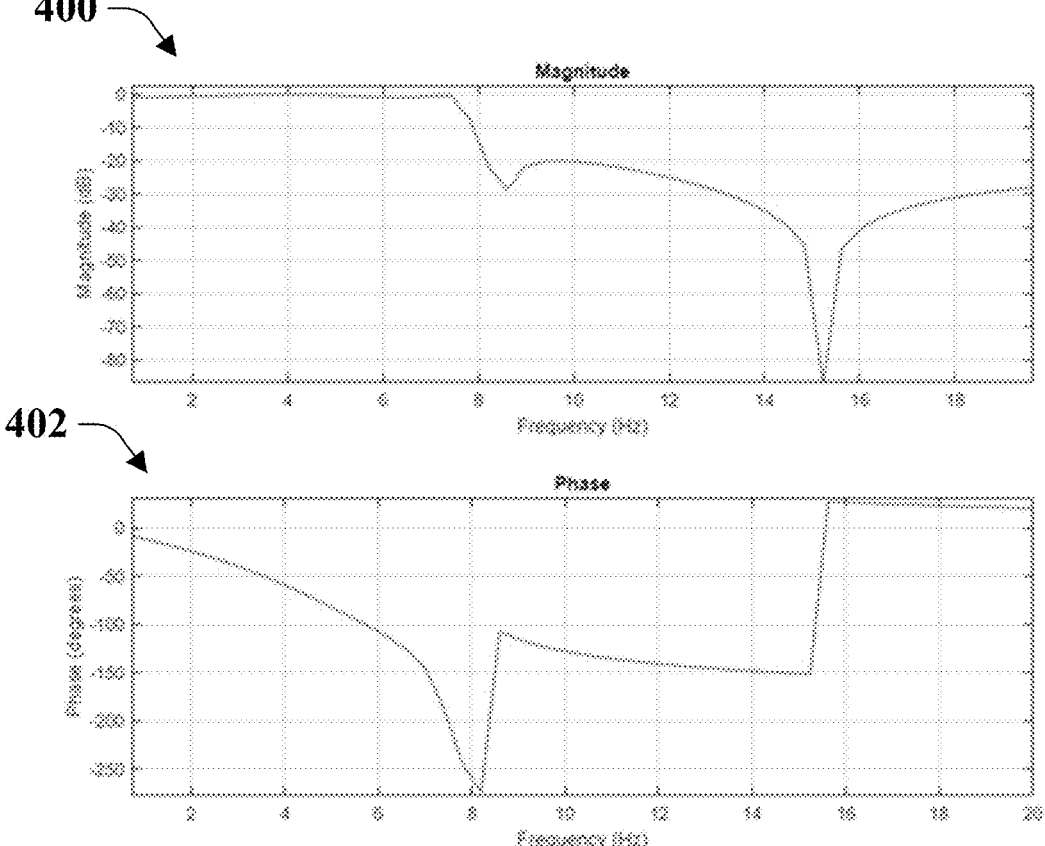
FIG. 4A depicts plots showing magnitude and phase characteristics of an exemplary accelerometer data filter.
Figure 4B:
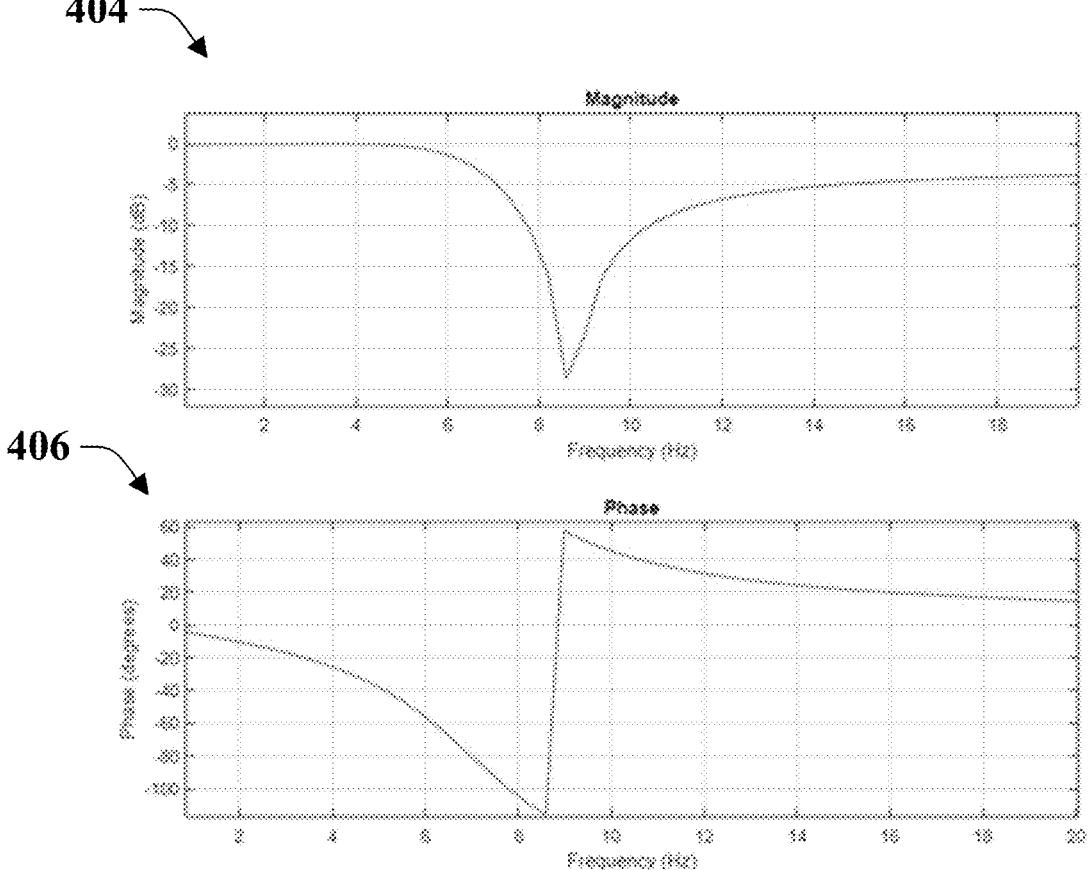
FIG. 4B depicts plots showing magnitude and phase characteristics of an exemplary accelerometer data filter.

With reference to FIG. 3, the motion data 300 can be processed with a first filter 302 and a second filter 304 to determine filtered motion data 306. Although this embodiment is depicted as having two filters, it should be appreciated that other embodiments can incorporate one filter or more than two filters. In one embodiment, the first filter 302 can be a $4^{th}$ order filter with a 7 Hz cutoff. The magnitude 400 and phase 402 characteristics of the exemplary first filter 302 can be seen in the plots depicted in FIG. 4A. The purpose of this filter is to remove machine noise, signal noise, and other high frequency noise that should be ignored in determining how to control the active mass damper. After the first filter 302, a second filter 304 can be used. In one embodiment, the second filter 304 is a $2^{nd}$ order filter with 4.5 Hz cutoff. The magnitude 404 and phase 406 characteristics of the exemplary second filter 304 can be seen in the plots depicted in FIG. 4B. The result of these two filters is filtered motion data 306 having a clean acceleration data signal from the 2 to 5 Hz range with gentle negative gains in the 5 to 6.5 Hz range and a hard cutoff at 7 Hz.

The controller 202 is further configured to further process the acceleration data by adjusting the acceleration data signal in phase to account for filter phase response and processing delays. The processed acceleration data can be utilized to derive information regarding the position of the C-arm 16. The controller 202 can include storage, which can hold a proportional-integral-derivative (PID) control functionality and associated tuning parameters. It should be appreciated that the PID controller can be tuned using sound engineering judgment based on each particular application. The controller 202 can, using the filtered acceleration data as an input to the PID controller, determine a scalar amount of force that should be applied, proportional to C-arm 16 velocity or momentum. Because the momentum is conserved in the C-Arm 16 frame of reference, the force to be applied by the mass damper assembly 210 can be described as follows:

$$m_c \cdot \dot{v} = -\vec{F} \cdot \sin(\omega t - \varphi)$$

such that the momentum of the C-arm 16 is conserved or offset in the direction of the C-arm axis 34.

The controller 202 is configured to control the linear motor 212, based on the filtered acceleration data and motor control tuning parameters, to move the mass 214 in a linear reciprocating path to provide a force having a magnitude and a phase configured to dampen at least a portion of the movement of the C-arm 16. The force vector generated by the mass damper assembly 210, is applied at a time interval determined by the position of the C-arm 16 motion and conserves or offsets the momentum of the C-arm 16 in the C-arm axis 34 thereby serving as an active damper to null and/or dampen unintended motion of the C-arm 16. More specifically the active mass damper system 200 applies a force that can be generally described as sinusoidal with respect to time, at the measured frequency of the C-arm 16 in the C-arm axis 34. To accomplish this, the controller 202 operates the motor driver 204 to drive the motor 212 in accordance with the output of the PID controller. It should be appreciated that the motor driver 204 can be a standalone component, or in certain embodiments, it can be incorporated into the controller 202. In one embodiment, the controller 202 is configured to control the linear motor 212 such that the magnitude of the force provided by the mass 214 is proportional to the magnitude of the filtered motion data and/or the controller 202 is configured to control the linear motor 212 such that the phase of the force is offset by 90-degrees from the motion data signal.

Figure 5:
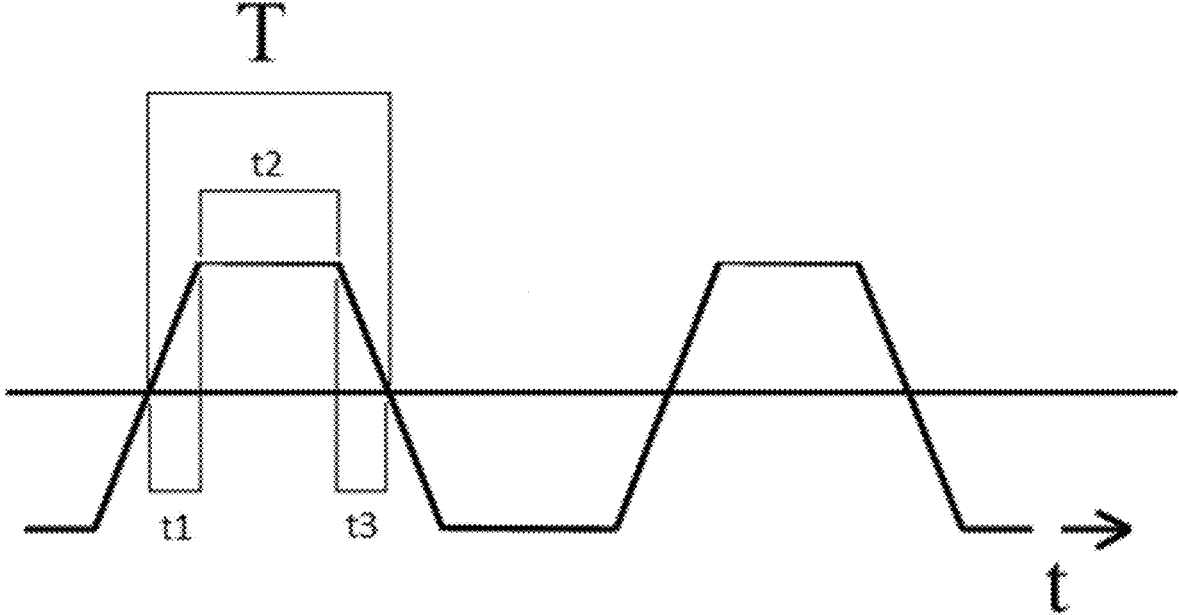
FIG. 5 is a graph of an exemplary motor control waveform.

In one embodiment, the motor driver 204 drives the motor 212 with a trapezoidal velocity profile to mimic the sinusoidal vibrations with minimal movement commands. FIG. 5 depicts a representative trapezoidal waveform, where T represents the total time for one movement, t1 is the period of acceleration, t2 is the coasting period, and t3 is the period of de-acceleration. The effects of the mass damper assembly 210 occur within the periods of acceleration and de-acceleration. To time the response successfully and dampen vibrations, the response should optimally be 90-degrees out of phase with the original signal from the one or more sensors 206. The response timing is determined from the filtered motion data (e.g. filtered acceleration data 306), but optimally should line up with the original data from the one or more sensors 206, which means that, as described above, the system must account for any phase offset caused by the filters (e.g. first and second filters 302, 304) as well as other offsets caused by physical and program limitations. Bode plots from the filter design phase can be used to account for filter phase shifts with respect to frequency, and other offset adjustments can be determined empirically when the system is tested.

In certain embodiments, the controller 202 is configured to determine whether or not to operate the mass damper assembly 210. For example, the controller 202 can analyze filtered acceleration data to determine whether a magnitude of the filtered acceleration data signal exceeds a predetermined threshold. If the magnitude of the filtered acceleration data signal does not exceed the predetermined threshold, then the linear motor 212 is deactivated or remains deactivated. If the magnitude does exceed the predetermined threshold, then the linear motor 212 is activated and controlled according to the PID controller based on the filtered acceleration data and motor control tuning parameters stored within the controller 202, until the magnitude is reduced to a level that falls below the predetermined threshold. In certain embodiments, the controller 202 can also determine a frequency of vibration of the filtered acceleration data. In these embodiments, the controller 202 analyzes both of the magnitude and the frequency of the filtered acceleration data signal. If both the magnitude exceeds the predetermined threshold and the frequency of the filtered acceleration data signal falls within a predetermined frequency range, then the linear motor 212 is activated. If one or both the magnitude does not exceed the predetermined threshold or the frequency of the filtered acceleration data signal does not fall within a predetermined frequency range, then the linear motor 212 is deactivated or remains deactivated.

Figures 6A, 6B:
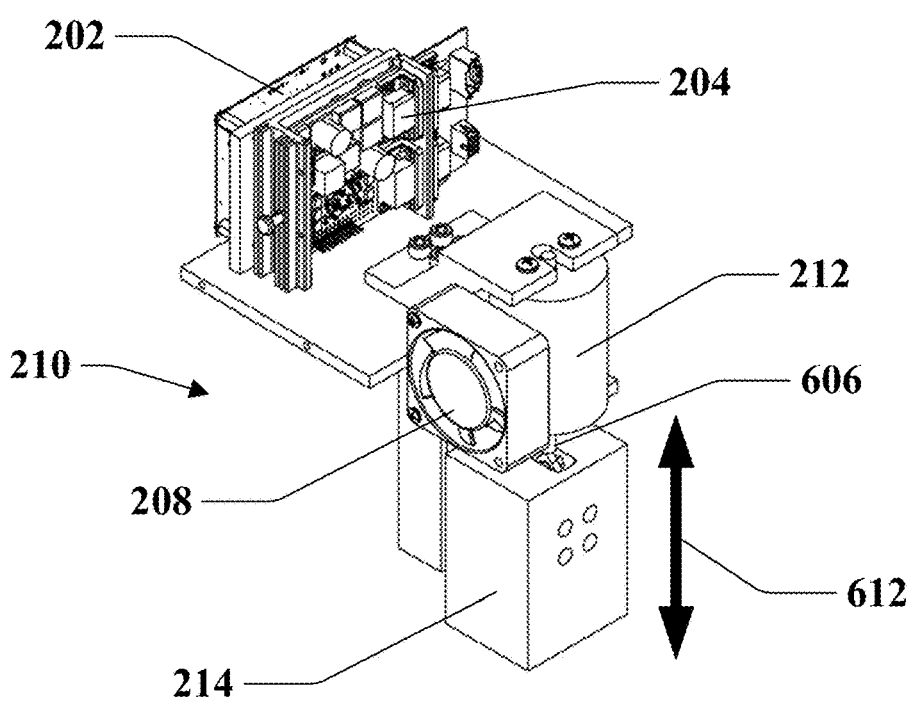
FIG. 6A is a perspective view of an exemplary mass damper assembly.
FIG. 6B is a side view of an exemplary mass damper assembly.

Turning now to FIGS. 6A and 6B, an exemplary mass damper assembly 210 is shown. The mass damper assembly 210 includes a linear motor 212 coupled to a mass 214. In certain embodiments, the linear motor 212 is coupled to the mass 214 by way of a coupler 606 such as a pin, a cable, or a rod, among others. The mass 214 can also be slidably coupled to a track 608 by way of a track guide 610. When the linear motor 212 is operated, it is configured to move the mass 214 back and forth in a reciprocating linear fashion along a mass axis 612, according to the control signals provided by the controller 202. The mass damper assembly 210 is coupled within the C-arm 16, for example, within a compartment located in the bottom tip 36 of the C-arm 16, such that the mass axis 612 is aligned with the C-arm axis 34, and remains aligned with the C-arm axis 34 regardless of the C-arm 16 position or angle. In certain embodiments, the mass 214 can be constructed from a metal such as steel. In one particular embodiment, the mass 214 has a weight of 5 pounds. It should be appreciated that the weight of the mass 214 can be selected using sound engineering judgment. The mass 214 can be any appropriate shape such as a rectangular prism, a cylinder, or a sphere, among others. In certain embodiments, the mass damper assembly 210 can also include the fan 208 positioned so that the fan 208 can cool the linear motor 212. In certain embodiments, the controller 202 and/or the motor driver 204 can be mounted to the mass damper assembly. The controller 202 and/or the motor driver 204 can be mounted, for example, on a chassis or mounting bracket coupled to the mass damper assembly 210.

Figure 7:
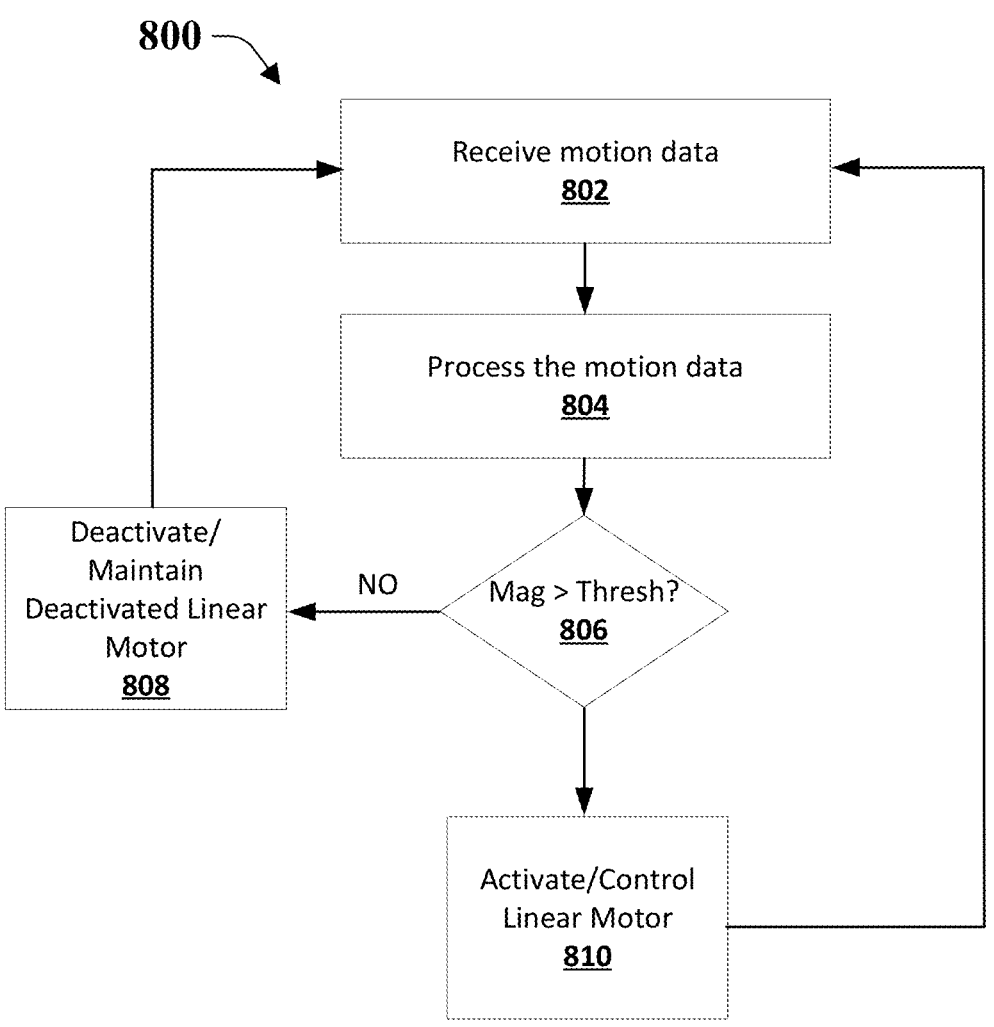
FIG. 7 is a flow diagram depicting a method of operating an active mass damper system.

A method 800 for operating the active mass damper system 200 is depicted in FIG. 7. At reference numeral 802, the controller 202 receives motion data (e.g. acceleration data) from one or more sensors 206. The motion data is representative of movement of the C-arm 16. At reference numeral 804, the controller 202 processes the motion data. During this processing step, the controller 202 filters the motion data to remove unwanted frequencies from the motion data. In certain embodiments, the controller 202 further processes the motion data after the filtering step in order to adjust and compensate for the filter phase response and processing delays. At reference numeral 806, the controller 202 analyzes the filtered motion data to determine whether the filtered motion data has an amplitude higher than a predetermined threshold. If the magnitude of the filtered motion data signal does not exceed the predetermined threshold, then the linear motor 212 is deactivated or remains deactivated at reference numeral 808. If the magnitude does exceed the predetermined threshold, then at reference numeral 810, the linear motor 212 is activated and/or controlled according to a PID controller based on the filtered motion data and motor control tuning parameters stored within the controller 202, until the amplitude of the filtered motion data signal is reduced to a level that falls below the predetermined threshold. The controller 202 controls the linear motor 212 in order to dampen undesired movement and/or vibrations of the C-arm 16 represented by the acceleration data, and the linear motor's 212 response is timed to be 90-degrees out of phase with the original signal from the one or more sensors 206.

Moreover, the word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, "at least one of A and B", or "at least one of A or B" and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features, ranges, and acts described above are disclosed as example forms of implementing the claims.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. An active mass damper system, comprising:
one or more sensors configured to detect motion of a C-arm and output corresponding motion data representative of the motion of the C-arm;
a mass damper assembly comprising:
a linear motor; and
a mass coupled to the linear motor; and
a controller configured to:
receive the motion data;
process the motion data by applying one or more filters to the motion data to create filtered motion data; and
control the linear motor, based on the filtered motion data and motor control tuning parameters, to move the mass in a linear reciprocating path to provide a force having a magnitude and a phase configured to dampen at least a portion of the motion of the C-arm.

2. The active mass damper system of claim 1, wherein the one or more sensors are one or more accelerometers, and the motion data is acceleration data.

3. The active mass damper system of claim 1, wherein the controller is further configured to process the motion data by compensating for at least one of a filter phase response from the one or more filters or processing delays.

4. The active mass damper system of claim 1, wherein the controller is further configured to analyze the filtered motion data to determine whether the filtered motion data has an amplitude higher than a predetermined threshold.

5. The active mass damper system of claim 4, wherein the controller is further configured to, upon determining that the amplitude of the filtered motion data does not exceed the predetermined threshold, deactivate the linear motor.

6. The active mass damper system of claim 4, wherein the controller is further configured to, upon determining that the amplitude of the filtered motion data exceeds the predetermined threshold, continue control of the linear motor until the amplitude of the filtered motion data is reduced to a level below the predetermined threshold.

7. The active mass damper system of claim 1, wherein the controller is configured to control the linear motor using a control signal having a trapezoidal velocity profile.

8. The active mass damper system of claim 1, wherein the controller is configured to control the linear motor such that the magnitude of the force provided by the mass is proportional to the magnitude of the filtered motion data.

9. The active mass damper system of claim 1, wherein the controller is configured to control the linear motor such that the phase of the force is offset by 90-degrees from the motion data.

10. The active mass damper system of claim 1, wherein the one or more filters are configured to suppress motion data frequencies that are above an upper frequency limit and/or below a lower frequency limit.

11. A method for operating an active mass damper system, comprising:
receiving motion data from one or more motion sensors located in a C-arm, wherein the motion data is representative of motion of the C-arm;

processing the motion data by applying one or more filters to the motion data to create filtered motion data; and controlling a linear motor, based on the filtered motion data and motor control tuning parameters, to move a mass in a linear reciprocating path to provide a force having a magnitude and a phase configured to dampen at least a portion of the motion of the C-arm.

12. The method of claim 11, wherein the one or more sensors are one or more accelerometers, and the motion data is acceleration data.

13. The method of claim 11, wherein processing the motion data further comprises compensating for at least one of a filter phase response from the one or more filters or processing delays.

14. The method of claim 11, further comprising:

analyzing the filtered motion data to determine whether the filtered motion data has an amplitude higher than a predetermined threshold.

15. The method of claim 14, further comprising:

deactivating the linear motor in response to determining that the amplitude of the filtered motion data does not exceed the predetermined threshold.

16. The method of claim 14, further comprising:

in response to determining that the amplitude of the filtered motion data exceeds the predetermined threshold, continuing control of the linear motor until the amplitude of the filtered motion data is reduced to a level below the predetermined threshold.

17. The method of claim 11, wherein controlling the linear motor includes communicating a control signal having a trapezoidal velocity profile.

18. The method of claim 11, wherein controlling the linear motor comprises controlling the linear motor such that the magnitude of the force provided by the mass is proportional to the magnitude of the filtered motion data.

19. The method of claim 11, wherein controlling the linear motor comprises controlling the linear motor such that the phase of the force is offset by 90-degrees from the motion data.

20. An imaging device comprising:

a C-arm supported by an attachment arm, wherein the c-arm comprises an imaging device and one or more sensors attached thereto configured to detect motion of the C-arm and output corresponding motion data representative of the motion of the C-arm;

a mass damper assembly comprising a linear motor and a mass coupled to the linear motor, wherein the mass damper assembly is located within a portion of the C-arm; and a controller configured to:

receive the motion data;

process the motion data by applying one or more filters to the motion data to create filtered motion data; and control the linear motor, based on the filtered motion data and motor control tuning parameters, to move the mass in a linear reciprocating path to provide a force having a magnitude and a phase configured to dampen at least a portion of the motion of the C-arm.

\* \* \* \* \*